United States Patent
Zieger et al.

(10) Patent No.: US 12,426,780 B2
(45) Date of Patent: Sep. 30, 2025

(54) PLACIDO PATTERN FOR A CORNEAL TOPOGRAPHER

(71) Applicant: Alcon Inc., Fribourg (CH)

(72) Inventors: Peter Zieger, Berlin (DE); Horia Grecu, Berlin (DE)

(73) Assignee: ALCON INC., Fribourg (CH)

( * ) Notice: Subject to any disclaimer, the term of this patent is extended or adjusted under 35 U.S.C. 154(b) by 656 days.

(21) Appl. No.: 17/505,701

(22) Filed: Oct. 20, 2021

(65) Prior Publication Data
US 2022/0125304 A1 Apr. 28, 2022

Related U.S. Application Data

(60) Provisional application No. 63/105,969, filed on Oct. 27, 2020.

(51) Int. Cl.
| | |
|---|---|
| *A61B 3/10* | (2006.01) |
| *A61B 3/00* | (2006.01) |
| *A61B 3/107* | (2006.01) |
| *A61B 3/14* | (2006.01) |

(52) U.S. Cl.
CPC ............ *A61B 3/107* (2013.01); *A61B 3/0008* (2013.01)

(58) Field of Classification Search
CPC ....... A61B 3/154; A61B 3/0025; A61B 3/107; A61B 3/0008; G01B 11/255
USPC .......................................................... 351/212
See application file for complete search history.

(56) References Cited

U.S. PATENT DOCUMENTS

| | | | |
|---|---|---|---|
| 6,116,738 A | 9/2000 | Rorabaugh | |
| 6,190,012 B1 * | 2/2001 | Ishikura | A61B 3/107 351/212 |
| 9,339,177 B2 * | 5/2016 | Grenon | A61B 3/0025 |
| 2001/0055095 A1 | 12/2001 | D'Souza | |
| 2004/0061833 A1 * | 4/2004 | Niven | A61B 3/107 351/212 |
| 2006/0132712 A1 | 6/2006 | Grove | |

(Continued)

FOREIGN PATENT DOCUMENTS

| | | |
|---|---|---|
| BR | PI0802388 A2 | 3/2010 |
| CN | 108498066 A * | 9/2018 |

(Continued)

OTHER PUBLICATIONS

"Placido ring image with overlapping rings." Image taken from https://www.bayeyecare.co.nz/dry-eye, accessed Sep. 7, 2021.

*Primary Examiner* — Mahidere S Sahle

(57) ABSTRACT

In certain embodiments, an ophthalmic system for determining the topography of the anterior surface of the cornea of an eye comprises an illuminator, a camera, and a computer. The illuminator illuminates the anterior surface of the cornea of the eye with a Placido pattern. The Placido pattern comprises a plurality of rings. A ring of the plurality of rings has a distinguishing feature that distinguishes the ring from an adjacent ring. The anterior surface of the cornea reflects the Placido pattern. The camera captures an image of the reflected Placido pattern. The computer: analyzes the image to detect a distortion of the ring that indicates an anomaly of the anterior surface of the cornea; identifies the ring of the plurality of rings according to the distinguishing feature of the ring; and generates the topography of the surface of the cornea that includes the anomaly.

18 Claims, 5 Drawing Sheets

(56) References Cited

U.S. PATENT DOCUMENTS

| | | | |
|---|---|---|---|
| 2010/0182568 A1* | 7/2010 | Sarver | A61B 3/107 351/212 |
| 2017/0042421 A1* | 2/2017 | Wallace | A61B 3/107 |
| 2022/0202287 A1* | 6/2022 | Dellagiacoma | A61B 3/13 |

FOREIGN PATENT DOCUMENTS

| | | | |
|---|---|---|---|
| EP | 0269269 A1 * | 6/1988 | |
| EP | 1824375 B1 | 8/2008 | |
| JP | 2006158749 A | 6/2006 | |

* cited by examiner

PLACIDO PATTERN FOR A CORNEAL TOPOGRAPHER

TECHNICAL FIELD

The present disclosure relates generally to corneal topographers, and more particularly to a Placido pattern for a corneal topographer.

BACKGROUND

Corneal topography describes the shape of corneal surfaces. For example, Placido topographers project a pattern of equally spaced concentric rings onto the anterior corneal surface and analyze the reflection of the rings to determine the shape of the surface. If the surface is an ideal sphere, the reflected rings match the projected pattern of equally spaced rings. If the surface has variations, areas where the reflected rings are closer together indicate steeper corneal curvature, and areas where the rings are farther part indicate flatter areas. In addition, distinct, well-formed rings indicate that the corneal surface is smooth.

Placido topographers rely on analyzing images of the reflected pattern, which can be difficult. In certain situations, known patterns are not easily analyzed.

BRIEF SUMMARY

In certain embodiments, an ophthalmic system for determining the topography of the anterior surface of the cornea of an eye comprises an illuminator, a camera, and a computer. The illuminator illuminates the anterior surface of the cornea of the eye with a Placido pattern. The Placido pattern comprises a plurality of rings. A ring of the plurality of rings has a distinguishing feature that distinguishes the ring from an adjacent ring. The anterior surface of the cornea reflects the Placido pattern. The camera captures an image of the reflected Placido pattern. The computer: analyzes the image to detect a distortion of the ring that indicates an anomaly of the anterior surface of the cornea; identifies the ring of the plurality of rings according to the distinguishing feature of the ring; and generates the topography of the surface of the cornea that includes the anomaly.

Embodiments may include none, one, some, or all of the following features:

The distinguishing feature of the ring that distinguishes the ring from the adjacent ring may comprise: a color of the ring that is different from a color of the adjacent ring; a thickness of the ring that is different from a thickness of the adjacent ring; and/or a separation between the ring and the adjacent ring that is different from a separation between the adjacent ring and a next ring.

The ring may have a marker feature that indicates a location on the ring. The computer may determine a location of the distortion on the ring according to the marker feature. The marker feature may comprise a gap in the ring or marking on the ring.

In certain embodiments, a Placido pattern for determining the topography of the anterior surface of the cornea of an eye comprises a plurality of rings. A ring of the plurality of rings has a distinguishing feature that distinguishes the ring from an adjacent ring. The ring also has a marker feature indicating a location on the ring.

Embodiments may include none, one, some, or all of the following features:

The distinguishing feature of the ring that distinguishes the ring from the adjacent ring may comprise: a color of the ring that is different from a color of the adjacent ring; a thickness of the ring that is different from a thickness of the adjacent ring; and/or a separation between the ring and the adjacent ring that is different from a separation between the adjacent ring and a next ring.

The marker feature may comprise a gap in the ring or marking on the ring.

In certain embodiments, a method for determining the topography of the anterior surface of the cornea of an eye, comprises illuminating the anterior surface of the cornea of the eye with a Placido pattern. The Placido pattern comprises a plurality of rings. A ring of the plurality of rings has a distinguishing feature that distinguishes the ring from an adjacent ring. The anterior surface of the cornea reflects the Placido pattern. An image of the reflected Placido pattern is captured. A computer performs the following: analyzing the image to detect a distortion of the ring that indicates an anomaly of the anterior surface of the cornea; identifying the ring of the plurality of rings according to the distinguishing feature of the ring; and generating the topography of the surface of the cornea that includes the anomaly.

Embodiments may include none, one, some, or all of the following features:

The distinguishing feature of the ring that distinguishes the ring from the adjacent ring may comprise: a color of the ring that is different from a color of the adjacent ring; a thickness of the ring that is different from a thickness of the adjacent ring; and/or a separation between the ring and the adjacent ring that is different from a separation between the adjacent ring and a next ring.

The ring may have a marker feature that indicates a location on the ring. The computer may perform the following: determining a location of the distortion on the ring according to the marker feature. The marker feature may comprise a gap in the ring or marking on the ring.

DESCRIPTION OF EXAMPLE EMBODIMENTS

Figure 1:
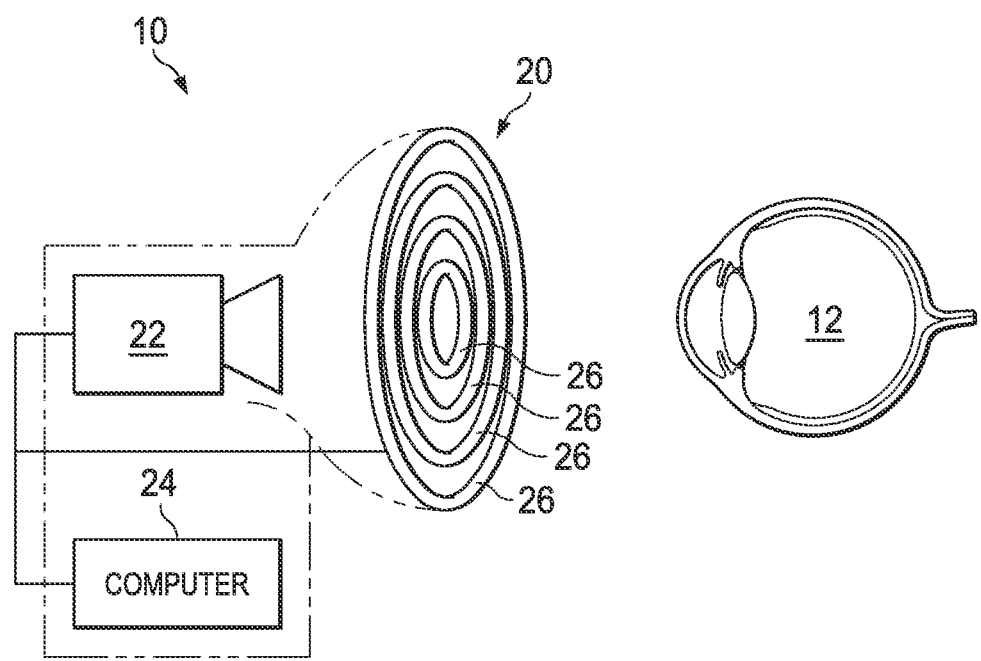
FIG. 1 illustrates an example of an ophthalmic system for determining the topography of the anterior surface of the cornea of an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Placido topographers rely on analyzing images of a reflected Placido pattern. Certain embodiments provide a Placido pattern that may be more easily analyzed. In the embodiments, a Placido pattern comprises a plurality of rings. At least one ring has a distinguishing feature that distinguishes the ring from an adjacent ring, which can be used to identify the ring. In addition, at least one ring also has a marker feature indicating a location on the ring, which can be used to identify the location on the ring.

FIG. 1 illustrates an example of an ophthalmic system 10 for determining the topography of the anterior surface of the cornea of an eye 12, according to certain embodiments. In the example, system 10 includes an illuminator 20, a camera 22, and a computer 24. As an overview of operation, illuminator 20 illuminates the anterior corneal surface with a Placido pattern. The Placido pattern comprises a plurality of concentric rings. At least one ring has a distinguishing feature that distinguishes the ring from an adjacent ring, and at least one ring has at least one marker feature indicating a location on the ring.

Continuing with the overview, the corneal surface reflects the Placido pattern. Camera 22 generates an image of the reflected Placido pattern. Computer 24 analyzes the image to detect a distortion of a ring, which typically indicates an anomaly of the corneal surface. Computer 24 identifies the ring with the distortion according to the distinguishing feature of the ring. For example, the ring may have a color, thickness, separation, and/or other suitable distinguishing feature that distinguishes the ring from an adjacent ring. Computer 24 determines the location of the distortion on the ring according to a marker feature. For example, the location may have a gap, marking, or other suitable marker feature that identifies the location on the ring. Computer 24 generates a topography of the corneal surface that includes the location of the anomaly.

Turning to the parts of system 10, illuminator 20 illuminates the anterior corneal surface with a Placido pattern, which may be referred to as an "illumination Placido pattern", or "illumination pattern", with "illumination rings". Examples of Placido patterns are described with reference to FIGS. 3A to 5. Illuminator 20 may comprise any suitable arrangement of one or more light sources configured to illuminate the corneal surface with a Placido pattern. In certain embodiments, illuminator 20 includes illuminator rings 26, where each illuminator ring 26 illuminates the corneal surface with a ring of the Placido pattern. In other embodiments, illuminator 20 includes pixel illuminators, where each pixel illuminates the corneal surface with a pixel of light. The pixels are combined to yield the Placido pattern. Computer 24 may turn on and off particular pixel illuminators to yield a specific Placido pattern.

The anterior corneal surface of eye 12 typically has a tear film. The tear film-air interface reflects the Placido pattern, which may be referred to as a "reflected Placido pattern", or "reflected pattern", with "reflected rings". The reflected Placido pattern can indicate the shape of the corneal surface. Camera 22 generates an image of the reflected Placido pattern. Camera 22 may be any suitable camera that captures and records images. For example, camera 22 may be a digital camera that includes: an image sensor that detects light reflected from an object; an image processor that converts sensor output to digital data representing the image; and a memory that records the digital data.

Computer 24 determines the topography of the corneal surface from an image of the reflected Placido pattern. Computer 24 detects a distortion of a reflected ring, which typically indicates an anomaly of the surface. If the surface is an ideal sphere, the reflected pattern should match the illumination pattern. If the surface has variations, the reflected pattern may have distortions from the illumination pattern. A distortion may be any suitable difference between the reflected pattern and the illumination pattern that indicates a difference in the anterior corneal surface from the expected surface, e.g., a spherical surface. For example, a distortion may be a difference in the separations between rings. Reflected rings that are closer together than the corresponding illumination rings indicate steeper corneal curvature. Reflected rings that are farther part than the corresponding illumination rings indicate flatter areas. As another example, the distortion may be a difference in the shapes of the rings. Reflected rings with a shape that is more oval or otherwise departs from that of the corresponding illumination rings may indicate an astigmatism. As another example, the distortion may be a difference in the edges of the rings. Reflected rings with distinct, focused edges indicate a smooth corneal surface. Reflected rings with edges that are wavy or otherwise depart from the edges of the corresponding illumination rings may indicate surface irregularities.

Computer 24 determines the location of the distortion in the reflected pattern to determine the location of the anomaly on the corneal surface. Locations of the reflected pattern correspond to locations of the anterior corneal surface. In certain embodiments, the illumination pattern is centered about an axis (e.g., visual or optical axis) of eye 12, and the reflected pattern is also centered about the axis. The image of the reflected pattern may include features of the eye (e.g., pupil, eyelids) to aid in matching the locations of the reflected pattern with the locations of the corneal surface.

In certain embodiments, computer 24 determines the location of the distortion by: (1) identifying the ring with the distortion, i.e., the distorted ring; and (2) determining the location of the distortion on the ring. In certain embodiments, computer 24 identifies the distorted ring according to a distinguishing feature of the ring. For example, the ring may have a color, thickness, separation, and/or other suitable distinguishing feature that distinguishes the ring from one or more other rings, e.g., an adjacent ring and/or other rings. The distinguishing feature may allow a user and/or an image processing logic to more readily identify the ring with the distortion.

Computer 24 determines the location of the distortion on the ring according to a marker feature. For example, the location may have a gap, marking, or other suitable marker feature that identifies a location on the ring. The marker feature may allow a user and/or an image processing logic to more readily identify the location of the distortion on the ring. After determining the location of the distortion in the reflected pattern, the location of the anomaly on the surface may be determined. Computer 24 generates the topography of the corneal surface, which includes the anomaly and the location of the anomaly.

Figure 2:
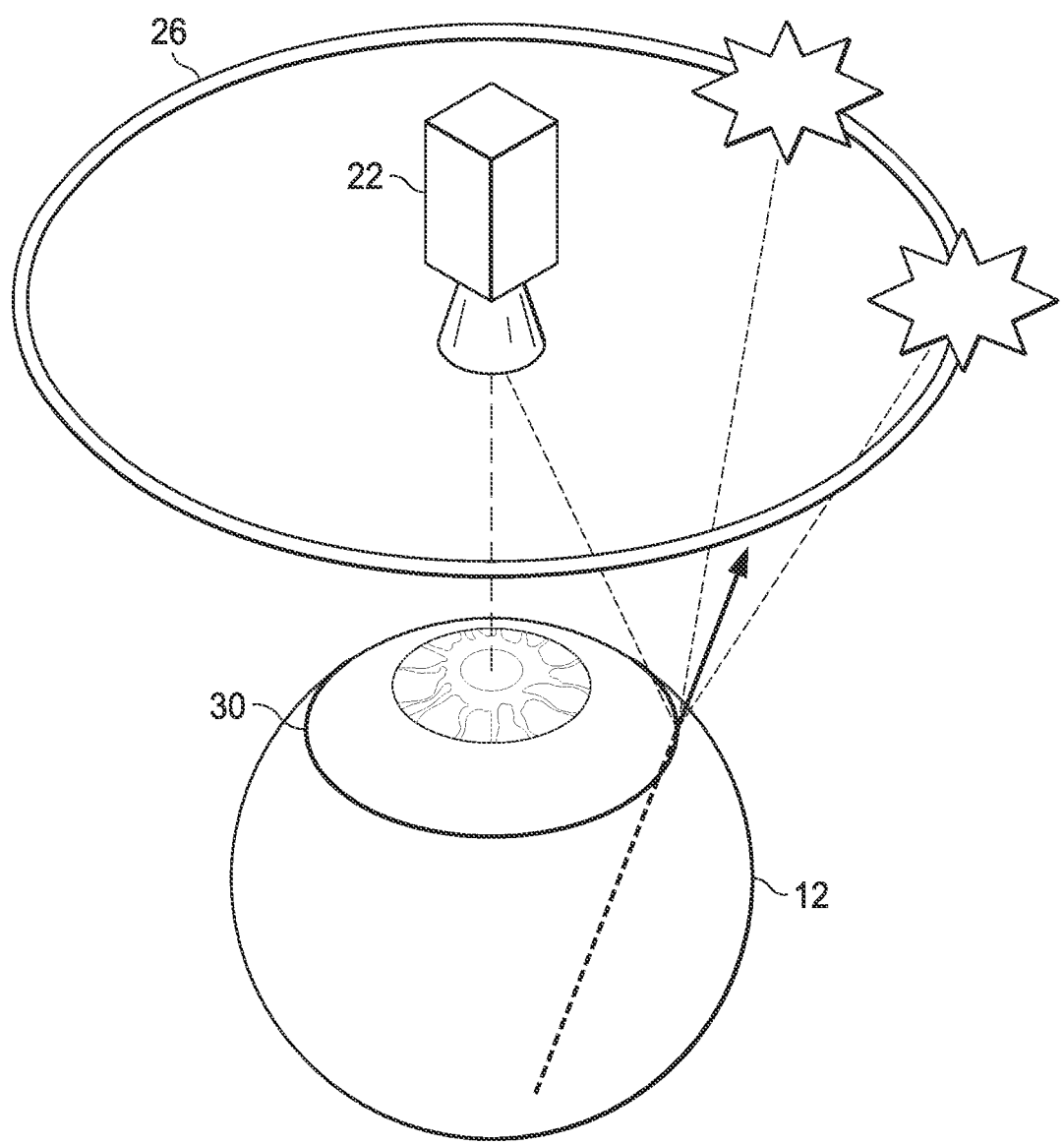
FIG. 2 illustrates an example of how an illuminator ring of the illuminator of the system of FIG. 1 illuminates an eye.

FIG. 2 illustrates an example of how an illuminator ring 26 of illuminator 20 illuminates eye 12. In the example, illuminator ring 26 illuminates a ring 30 of a Placido pattern onto the anterior corneal surface of eye 12. The surface reflects ring 30. Camera 22 detects the reflected ring 30. If the surface that reflects ring 30 does not have any anomalies, the reflected ring 30 detected by camera 22 will have an expected shape, e.g., a shape that generally matches the shape of illumination ring 30 prior to reflection. That is, the anterior surface does not distort ring 30. If the surface that reflects ring 30 has an anomaly, the reflected ring 30 detected by camera 22 may have a distortion that indicates the presence of the anomaly.

Figure 3A:
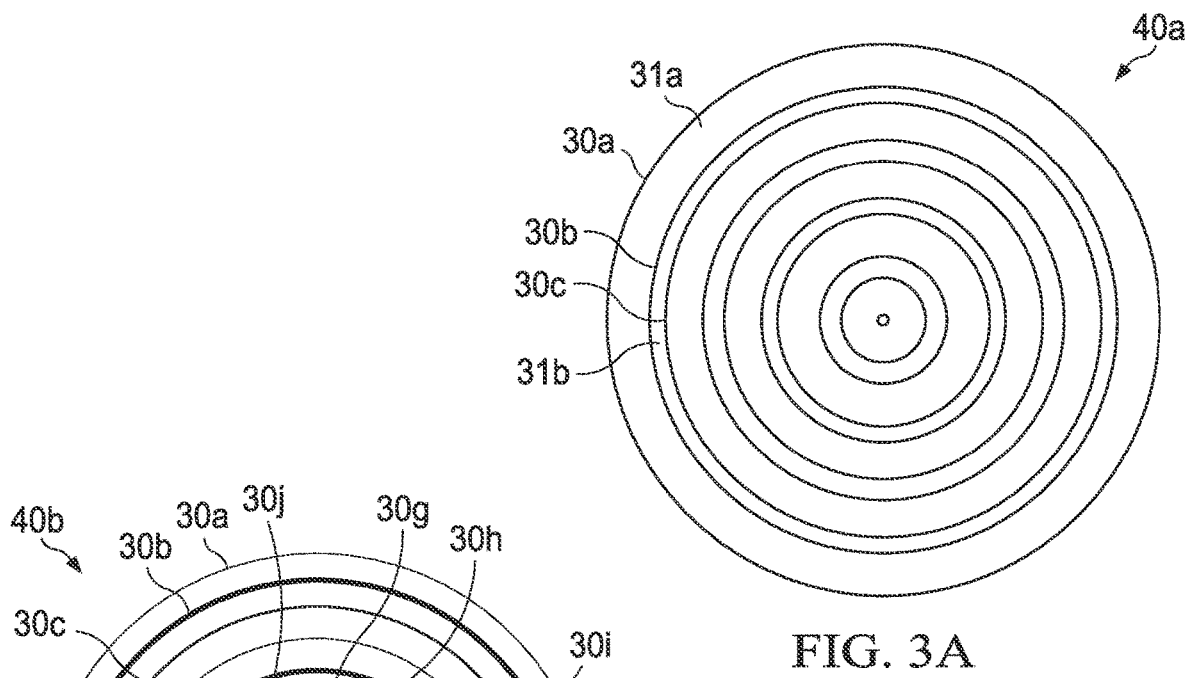
FIGS. 3A to 3C illustrate examples of Placido patterns with rings having a distinguishing feature that distinguishes the ring from an adjacent ring.
Figure 3B:
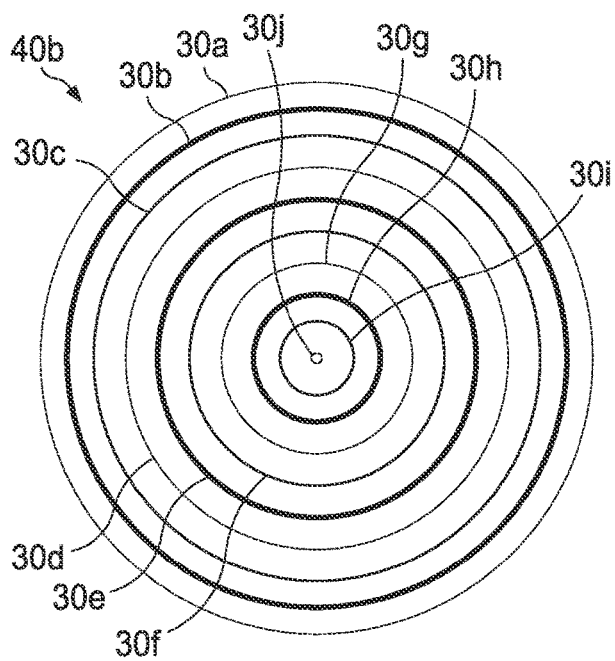
Figure 3C:
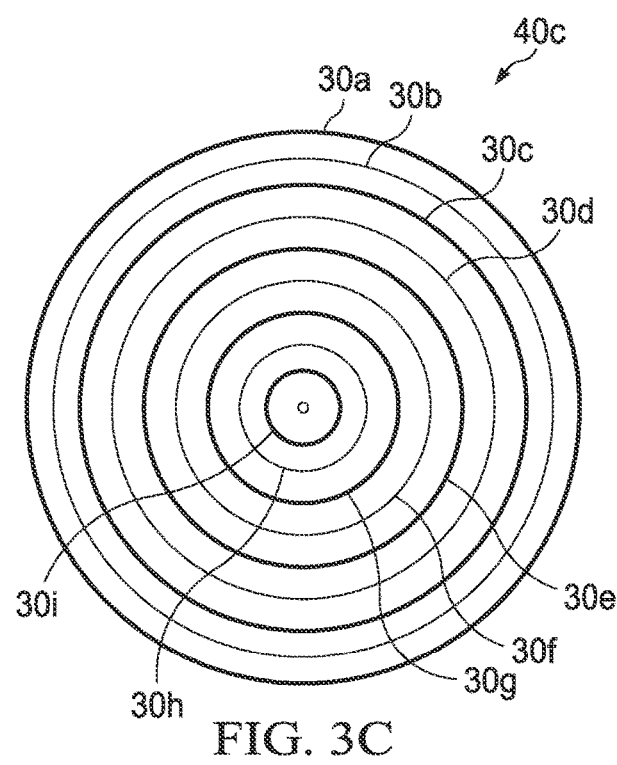

FIGS. 3A to 3C illustrate examples of Placido patterns 40 (40a-40c) with rings 30 having a distinguishing feature that distinguishes the ring from an adjacent ring. A distinguishing feature has a suitable color, dimension, arrangement, and/or other feature that allows a user and/or software to distinguish a ring from one or more other rings, e.g., a ring from an adjacent ring.

FIG. 3A illustrates a Placido pattern 40a with rings 30 that have different separations between adjacent rings 30. In the example, the separation 31a between rings 30a and 30b is greater than the separation 31b between rings 30b and 30c.

FIG. 3B illustrates a Placido pattern 40b with rings 30 that have different colors. Although not evident in the black and white drawing, rings 30a, 30d, 30g, and 30j are red; rings 30b, 30e, and 30h are blue; and rings 30c, 30f, and 30i are green. In certain embodiments, a sequence of a set number of adjacent rings 30 may have sequence of different colors. The sequence of colors may repeat for the next set number of rings. In the example, a sequence of three adjacent rings 30a, 30b, 30c has a sequence of different colors, red, blue, and green. That is, ring 30a is red, ring 30b is blue, and ring 30c is green. The sequence of colors repeats for the next three rings 30d, 30e, 30f.

FIG. 3C illustrates a Placido pattern 40c with rings 30 that have different thicknesses. In certain embodiments, a sequence of a set number of adjacent rings 30 may have sequence of different thicknesses. The sequence of thicknesses may repeat for the next set number of rings. In the example, a sequence of two adjacent rings 30a, 30b has a sequence of different thicknesses. The sequence of thicknesses repeats for the next two rings 30c, 30d.

Figure 4A:
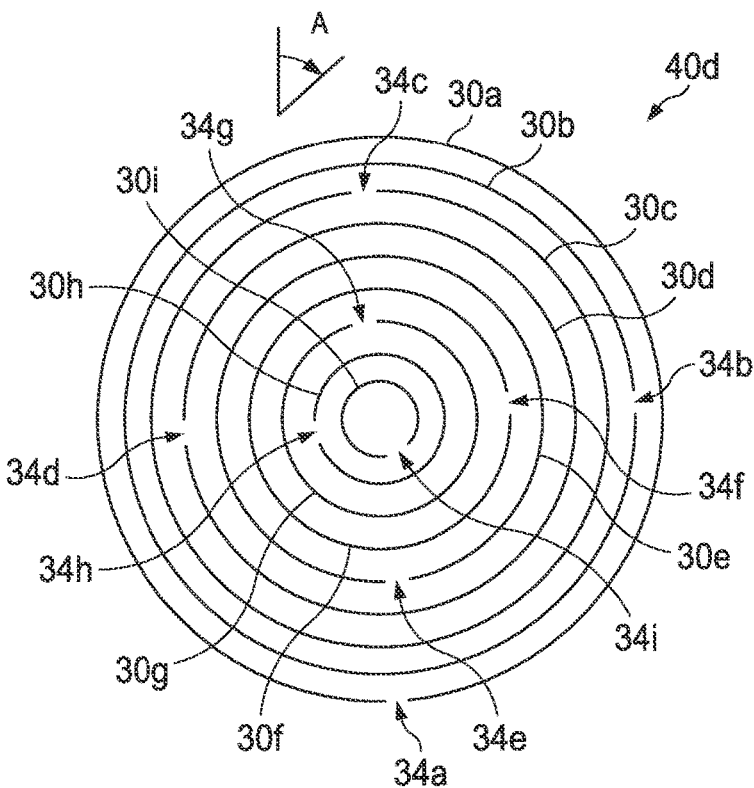
FIGS. 4A and 4B illustrates examples of Placido patterns with rings having a marker feature that identifies a location on the ring.
Figure 4B:
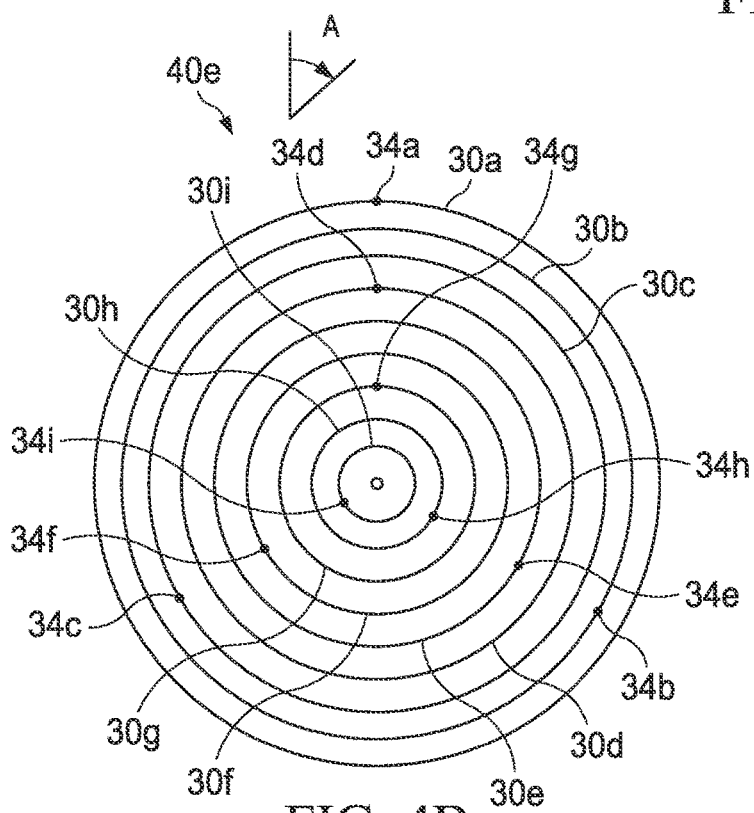

FIGS. 4A and 4B illustrates examples of Placido patterns 40 (40d-40e) with rings 30 having a marker feature 34 that identifies a location on the ring. A ring 30 with a marker feature 34 may be referred to as a marked ring 30.

FIG. 4A illustrates a Placido pattern 40d with rings 30 that have a marker feature 34 comprising a gap 34a-34i. A gap may have any suitable length that is detectable by a user and/or software to identify a location on a ring 30, e.g., a length with a value in the range of 0.5 to 1, 1 to 1.5, 1.5 to 2, and/or 2 to 5 millimeters. In certain embodiments, a sequence of a set number of adjacent rings 30 may have the marker feature 34 placed, e.g., equidistant, from each other in the sequence. The sequence of marker features 34 may repeat for the next set number of rings. For ease of explanation, let angle A have a vertex at the center of rings 30 and a direction as noted in the drawing. In the example, a sequence of four adjacent rings 30a-30d have gaps 34a-34d equidistant, from each other. That is, gap 34a is at approximately 180°, gap 34b is at approximately 90°, gap 34c is at approximately 0°, and gap 34d is at approximately 270°. The sequence of gaps 34e-34h repeats for rings 30e-30h.

FIG. 4B illustrates a Placido pattern 40e with rings 30 that have a marker feature 34 comprising a marking. A marking may have any suitable shape and size that is detectable by a user and/or software to identify a location on a ring 30. For example, a marking may have an average diameter with a value in the range of 0.5 to 1, 1 to 1.5, 1.5 to 2, and/or 2 to 5 millimeters. Example shapes include a circle, a polygon (e.g., square, rectangle), and a star.

In the example, the marking is a dot 34a-34i, and a sequence of three adjacent rings 30a-30c have dots 34a-34c equidistant, from each other. That is, dot 34a is at approximately 0°, dot 34b is at approximately 120°, and dot 34c is at approximately 240°. The sequence of dots 34d-34f repeats for rings 30d-30f.

Figure 5:
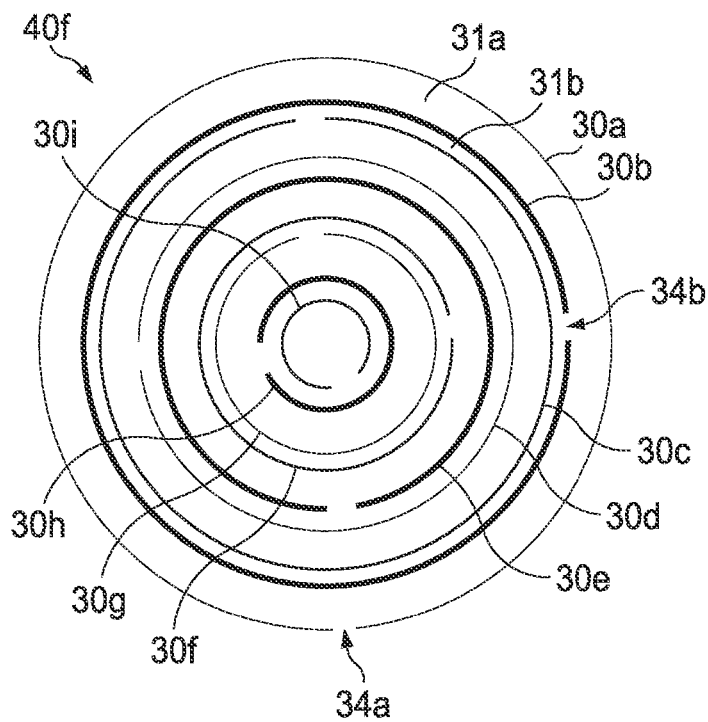
FIG. 5 illustrates an example of a Placido pattern with rings having one or more distinguishing features and/or one or more marker features.

FIG. 5 illustrates an example of a Placido pattern 40 (40f) with rings 30 (30a-30i) having one or more distinguishing features and/or one or more marker features 34. Although not evident in the black and white drawing, rings 30a, 30d, and 30g are red; rings 30b, 30e, and 30h are blue; and rings 30c, 30f, and 30i are green. In the example, rings 30 have different colors and separations 31 that distinguish them from at least adjacent rings 30. In addition, rings 30 have gaps 34 that identify a location on a ring. In certain embodiments, a ring 30 may have a distinguishing feature, a marker feature, neither, or both.

Figure 6:
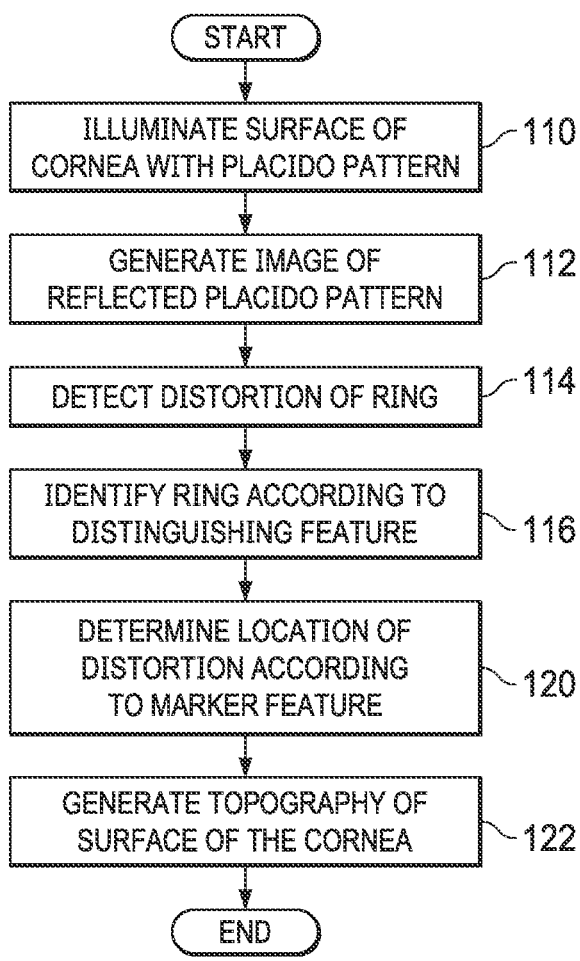
FIG. 6 illustrates an example of a method that may be performed by the system of FIG. 1, according to certain embodiments.

FIG. 6 illustrates an example of a method that may be performed by system 10 of FIG. 1, according to certain embodiments. In the embodiments, computer 24 may perform certain steps by sending instructions to components of system 10.

The method starts at step 110, where illuminator 20 illuminates the corneal surface with a Placido pattern. The Placido pattern comprises a plurality of rings. At least one ring has a distinguishing feature that distinguishes the ring from an adjacent ring, and at least one ring has a marker feature indicating a location on the ring. The corneal surface reflects the Placido pattern.

Camera 22 detects the reflected Placido pattern and generates an image of the reflected Placido pattern at step 112. Computer 24 analyzes the image to detect a distortion of a ring at step 114. The distortion typically indicates an anomaly of the corneal surface. Computer 24 identifies the ring according to distinguishing feature at step 116. For example, the ring may have a color, thickness, separation, and/or other suitable distinguishing feature that distinguishes the ring from an adjacent ring. Computer 24 determines the location of the distortion according to marker feature at step 120. For example, the location may have a gap, marking, or other suitable marker feature that identifies a location on the ring. Computer 24 generates the topography of the corneal surface at step 122. The topography describes the anomaly and the location of the anomaly. Computer 24 may output the topography via a user interface, e.g., a display. The method then ends.

A component (such as the computer 24) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed is:

1. An ophthalmic system for determining a topography of an anterior surface of a cornea of an eye, the system comprising:
    an illuminator configured to illuminate the anterior surface of the cornea of the eye with a Placido pattern, the Placido pattern comprising a plurality of rings that are discretely spaced and concentric, a ring of the plurality of rings having a distinguishing feature that distinguishes the ring from an adjacent ring, the anterior surface of the cornea reflecting the Placido pattern;
    a camera configured to capture an image of the reflected Placido pattern; and
    a computer configured to:
        analyze the image to detect a distortion of the ring, the distortion indicating an anomaly of the anterior surface of the cornea;
        identify the ring of the plurality of rings according to the distinguishing feature of the ring; and
        generate the topography of the surface of the cornea that includes the anomaly;
    wherein the ring has a single marker feature at a single location indicating a location on the ring, wherein the plurality of rings includes at least two successive adjacent rings without the marker feature followed by a third ring with the marker feature followed by at least two further successive adjacent rings without the marker feature; and
    the computer configured to:
        determine a location of the distortion on the ring according to the marker feature.

2. The ophthalmic system of claim 1, wherein the distinguishing feature of the ring that distinguishes the ring from the adjacent ring comprises:
    a color of the ring that is different from a color of the adjacent ring.

3. The ophthalmic system of claim 1, wherein the distinguishing feature of the ring that distinguishes the ring from an adjacent ring comprises:
    a thickness of the ring that is different from a thickness of the adjacent ring.

4. The ophthalmic system of claim 1, wherein the distinguishing feature of the ring that distinguishes the ring from an adjacent ring comprises:
    a separation between the ring and the adjacent ring that is different from a separation between the adjacent ring and a next ring.

5. The ophthalmic system of claim 1, wherein the marker feature of the ring comprises:
    a gap in the ring.

6. The ophthalmic system of claim 1, wherein the marker feature of the ring comprises:
    a marking on the ring.

7. A Placido pattern for determining a topography of an anterior surface of a cornea of an eye, the Placido pattern comprising:
    a plurality of rings that are discretely spaced and concentric, a ring of the plurality of rings having a distinguishing feature that distinguishes the ring from an adjacent ring, the ring having a single marker feature indicating a single location on the ring;
    wherein each successive concentric ring of the plurality of rings has the single marker feature placed at a different radial position than at least two successive adjacent rings.

8. The Placido pattern of claim 7, wherein the distinguishing feature of the ring that distinguishes the ring from the adjacent ring comprises:
    a color of the ring that is different from a color of the adjacent ring.

9. The Placido pattern of claim 7, wherein the distinguishing feature of the ring that distinguishes the ring from an adjacent ring comprises:
    a thickness of the ring that is different from a thickness of the adjacent ring.

10. The Placido pattern of claim 7, wherein the distinguishing feature of the ring that distinguishes the ring from an adjacent ring comprises:
    a separation between the ring and the adjacent ring that is different from a separation between the adjacent ring and a next ring.

11. The Placido pattern of claim 7, wherein the marker feature of the ring comprises:
    a gap in the ring.

12. The Placido pattern of claim 7, wherein the marker feature of the ring comprises:
    a marking on the ring.

13. A method for determining a topography of an anterior surface of a cornea of an eye, the method comprising:
    illuminating the anterior surface of the cornea of the eye with a Placido pattern, the Placido pattern comprising a plurality of rings that are discretely spaced and concentric, a ring of the plurality of rings having a distinguishing feature that distinguishes the ring from an adjacent ring, the anterior surface of the cornea reflecting the Placido pattern, the ring including a single marker feature at a single location indicating a location on the ring, the plurality of rings including at least two successive adjacent rings without the marker feature followed by a third ring with the marker feature followed by at least two further successive adjacent rings without the marker feature;

capturing an image of the reflected Placido pattern; and performing, by a computer, the following:

analyzing the image to detect a distortion of the ring, the distortion indicating an anomaly of the anterior surface of the cornea;

identifying the ring of the plurality of rings according to the distinguishing feature of the ring;

determining a location of the distortion on the ring according to the marker feature; and generating the topography of the surface of the cornea that includes the anomaly.

14. The method of claim 13, wherein the distinguishing feature of the ring that distinguishes the ring from the adjacent ring comprises:

a color of the ring that is different from a color of the adjacent ring.

15. The method of claim 13, wherein the distinguishing feature of the ring that distinguishes the ring from an adjacent ring comprises:

a thickness of the ring that is different from a thickness of the adjacent ring.

16. The method of claim 13, wherein the distinguishing feature of the ring that distinguishes the ring from an adjacent ring comprises:

a separation between the ring and the adjacent ring that is different from a separation between the adjacent ring and a next ring.

17. The method of claim 13, wherein the marker feature of the ring comprises:

a gap in the ring.

18. The method of claim 13, wherein the marker feature of the ring comprises:

a marking on the ring.

* * * * *